(12) United States Patent
Kim et al.

(10) Patent No.: US 9,755,161 B2
(45) Date of Patent: Sep. 5, 2017

(54) ORGANIC LIGHT EMITTING DISPLAY DEVICE

(71) Applicant: LG Display Co., Ltd., Seoul (KR)

(72) Inventors: DoHan Kim, Gyeonggi-do (KR); JungKeun Kim, Seoul (KR); Hyoseok Kim, Daejeon (KR); Min Yun, Gyeonggi-do (KR); SeungHee Yoon, Seoul (KR)

(73) Assignee: LG Display Co., Ltd., Seoul (KR)

( * ) Notice: Subject to any disclaimer, the term of this patent is extended or adjusted under 35 U.S.C. 154(b) by 175 days.

(21) Appl. No.: 14/919,944

(22) Filed: Oct. 22, 2015

(65) Prior Publication Data
US 2016/0164003 A1 Jun. 9, 2016

(30) Foreign Application Priority Data
Dec. 5, 2014 (KR) ........................ 10-2014-0174305

(51) Int. Cl.
*H01L 51/54* (2006.01)
*H01L 51/00* (2006.01)
(Continued)

(52) U.S. Cl.
CPC ........ *H01L 51/0072* (2013.01); *C07D 223/14* (2013.01); *C07D 223/32* (2013.01); *C07D 403/04* (2013.01); *C07D 409/10* (2013.01); *C09K 11/025* (2013.01); *C09K 11/06* (2013.01); *H01L 51/0052* (2013.01); *H01L 51/0056* (2013.01); *H01L 51/0058* (2013.01); *H01L 51/0067* (2013.01); *H01L 51/0074* (2013.01); *C09K 2211/1007* (2013.01); *C09K 2211/1011* (2013.01); *C09K 2211/1029* (2013.01); *C09K 2211/1059* (2013.01); *C09K 2211/1092* (2013.01); *C09K 2211/185* (2013.01); *H01L 51/0085* (2013.01); *H01L 51/5016* (2013.01); *H01L 51/5072* (2013.01)

(58) Field of Classification Search
CPC ............ H01L 51/0072; H01L 51/0056; H01L 51/0067; H01L 51/0074; H01L 51/0085; H01L 51/5016; H01L 51/5072; C07D 223/14; C07D 403/04; C07D 409/10; C09K 11/025; C09K 2211/1007; C09K 2211/1029; C09K 2211/185; C09K 2211/1011; C09K 2211/1059; C09K 2211/1092
USPC .......................................................... 428/54
See application file for complete search history.

(56) References Cited

U.S. PATENT DOCUMENTS

2007/0176541 A1 8/2007 Son et al.

FOREIGN PATENT DOCUMENTS

WO 00/33617 A1 6/2000
WO 2011/006574 A1 1/2011

OTHER PUBLICATIONS

Extended European Search Report issued in corresponding European Patent Application No. 15182869.6 dated Jan. 19, 2016.

*Primary Examiner* — Jayne Mershon
(74) *Attorney, Agent, or Firm* — Morgan, Lewis & Bockius LLP

(57) ABSTRACT

An organic light emitting display device is disclosed. The organic light emitting display device comprises an anode, an organic layer over the anode, and a cathode over the organic layer. The organic layer may include a heterocyclic compound. Alternatively, the organic layer may include a spirobisfluorene compound with hole transfer properties and a material with electron transfer properties.

9 Claims, 3 Drawing Sheets

(51) Int. Cl.
*C07D 223/14* (2006.01)
*C07D 403/04* (2006.01)
*C07D 409/10* (2006.01)
*C09K 11/06* (2006.01)
*C07D 223/32* (2006.01)
*C09K 11/02* (2006.01)
*H01L 51/50* (2006.01)

ORGANIC LIGHT EMITTING DISPLAY DEVICE

This application claims the priority benefit of Korean Patent Application No. 10-2014-0174305 filed on Dec. 5, 2014, which is incorporated herein by reference for all purposes as if fully set forth herein.

BACKGROUND

Field of the Invention

The present invention relates to a heterocyclic compound and an organic light emitting display device comprising the same, and more particularly, to a heterocyclic compound which is capable of reducing the operating voltage of an organic light emitting display device and improving its efficiency and lifetime and an organic light emitting display device comprising the same.

Discussion of Related Art

With the development of multimedia, panel displays are becoming more and more important. Accordingly, a variety of panel displays such as liquid crystal display (LCDs), plasma display panels (PDPs), field emission displays (FEDs), organic light emitting display devices, and the like are put to practical use.

Among them, the organic light emitting display devices are advantageous in that they can be formed on a flexible transparent substrate, such as plastic, can be driven at a low voltage of 10 V or less, have relatively low power consumption, and excellent color sensitivity, as compared to a plasma display panel or inorganic light emitting diode display. Further, the organic light emitting display device can represent three colors of green, blue and red, and thus is drawing a great deal of attention as a next-generation full-color display device.

An organic light emitting display device can be formed by sequentially forming an anode, a hole injection layer, a hole transport layer, a light emitting layer, and electron transport layer, an electron injection layer, and a cathode. For a luminescent material, excitons are formed by the recombination of electrons and holes injected from the two electrodes. Singlet excitons and triplet excitons are involved in fluorescence and phosphorescence, respectively. In recent years, there is a growing trend that phosphorescent materials are replacing fluorescent materials. For a fluorescent material, singlet excitons, which make up only 25% of all excitons formed in the light emitting layer, are used to produce light, and triplet excitons, which make up 75% of the excitons, are mostly lost and transformed into heat. Phosphorescent materials, in contrast, have a light emission mechanism for converting both singlet and triplet excitons into light.

A light emitting process of a phosphorescent material will be discussed briefly. Holes injected from the anode and electrons injected from the cathode meet in a host material of the emission layer. Though a hole and an electron may be paired in a dopant in some cases, a large amount of holes and electrons meet in the host in most cases due to high concentration of the host. At this point, the singlet excitons formed in the host transfer energy to the singlets or triplets of the dopant, while the triplet excitons transfer energy to the triplets of the dopant.

Since the excitons transferred to the singlets of the dopant are transferred to the triplets of the dopant by intersystem crossing, the first destination of all the excitons is a triplet level of the dopant. The thus-formed excitons are transferred to the ground state, and emit light. If the triplet energy of the hole transport layer or electron transport layer adjacent to the front and back of the light emitting layer is less than the triplet energy of the dopant, backward energy transfer takes place from the dopant or host to these layers, and this leads to an abrupt decrease in efficiency. Accordingly, the triplet energy of the hole/electron transport layers, as well as the host material of the light emitting layer, plays a very important role in phosphorescent devices.

For efficient energy transfer from the host to the dopant, the triplet energy of the host must be greater than the triplet energy of the dopant. For green light emission, the triplet energy of the host must be equal to or greater than 2.5 eV as long as the triplet energy of the dopant is 2.4 eV or greater, in order to facilitate energy transfer. However, materials with high triplet energy cause deteriorations of the device, including a decrease in device efficiency and a voltage rise. Materials with low thermal stability and low electric stability can decrease the lifetime of the device. Accordingly, there is a need for the development of novel phosphorescent materials with superior thermal stability and superior electric stability.

SUMMARY

Accordingly, the present invention is directed to an organic light emitting display device that substantially obviates one or more of the problems due to limitations and disadvantages of the related art.

An object of the present invention is to provide a heterocyclic compound which is capable of reducing the operating voltage of an organic light emitting display device and improving its efficiency and lifetime and an organic light emitting display device comprising the same.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, a heterocyclic compound may be represented by the following Chemical Formula 1:

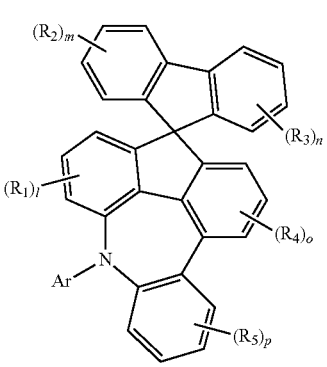

[Chemical Formula 1]

where $R_1$ to $R_5$ are independently one among hydrogen, deuterium, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l and o are an integer between 0 and 3, and m, n, and p are an integer between 0 and 4, wherein, if any of l, m, n, o, and p has a value of 2 or more, the corresponding R is the same with each other or any of l, m, n, o, and p has a value of 2 or more, the corresponding R is different from each other, and Ar is a substituted or unsubstituted aryl group having 6 to 30 carbon atoms or a substituted or unsubstituted heteroaryl group having 2 to 30 carbon atoms.

The heterocyclic compound includes one among the following compounds:

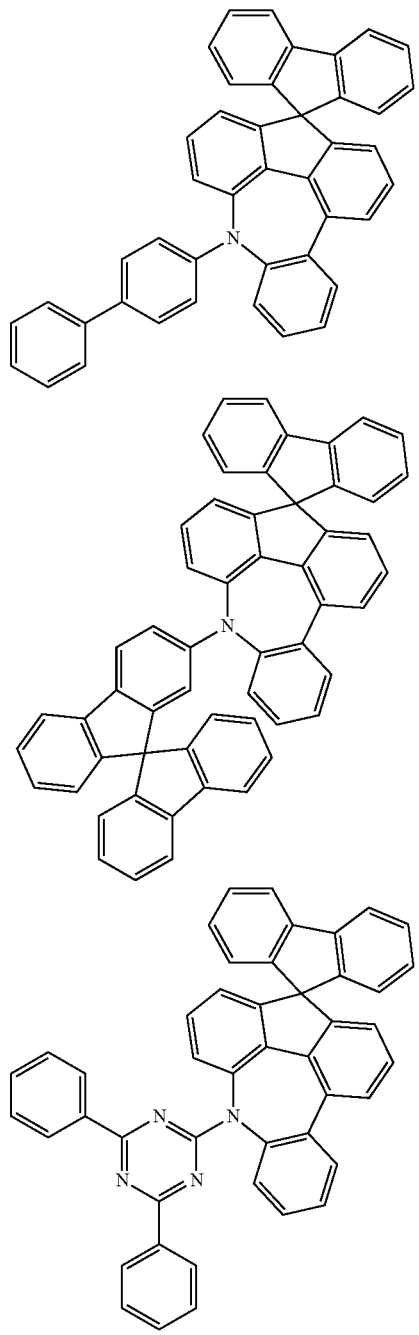

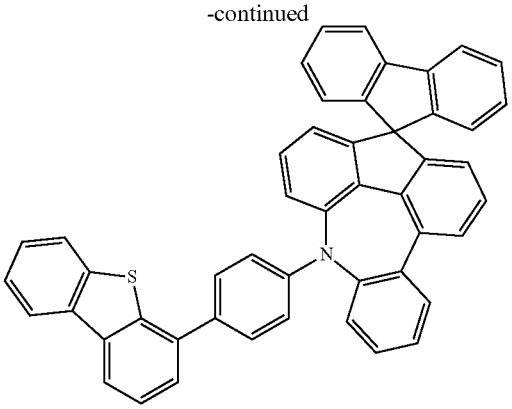

In another aspect, an organic light emitting display device comprises an anode; an organic layer on the anode; and a cathode on the organic layer, wherein the organic layer includes the heterocyclic compound.

The organic layer includes a light emitting layer.

A host for the light emitting layer includes the heterocyclic compound.

The organic layer includes at least one among a hole transport layer, an electron blocking layer, a hole blocking layer, and an electron transport layer, and at least one among the hole transport layer, the electron blocking layer, the hole blocking layer, and the electron transport layer includes the heterocyclic compound.

In another aspect, an organic light emitting display device comprises an organic layer on an anode; and a cathode on the organic layer, wherein the organic layer includes a spirobisfluorene compound with hole transfer properties and a material with electron transfer properties.

The material with electron transfer properties includes a heteroaryl group.

The organic layer includes a light emitting layer.

The organic layer includes a host for the light emitting layer.

The light emitting layer includes a host and a dopant, and the triplet energy of the organic layer in the host is equal to or greater than 2.5 eV.

An organic light emitting display device having the compound has a higher triplet energy, reduced operating voltage, and increased lifetime, as compared with an organic light emitting display device without the compound.

The organic layer comprises at least one among a hole transport layer, an electron blocking layer, a hole blocking layer, and an electron transport layer, and the at least one among the hole transport layer, the electron blocking layer, the hole blocking layer, and the electron transport layer includes the compound.

The compound includes a compound represented by the following Chemical Formula 1:

[Chemical Formula 1]

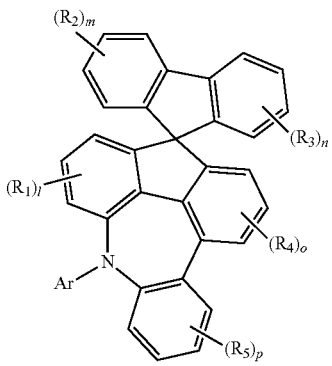

where R₁ to R₅ are independently one among hydrogen, deuterium, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l and o are an integer between 0 and 3, and m, n, and p are an integer between 0 and 4, wherein, if any of l, m, n, o, and p has a value of 2 or more, the corresponding R is the same with each other any of l, m, n, o, and p has a value of 2 or more, the corresponding R is or different form each other, and Ar is a substituted or unsubstituted aryl group having 6 to 30 carbon atoms or a substituted or unsubstituted heteroaryl group having 2 to 30 carbon atoms.

The compound includes one among the following compounds:

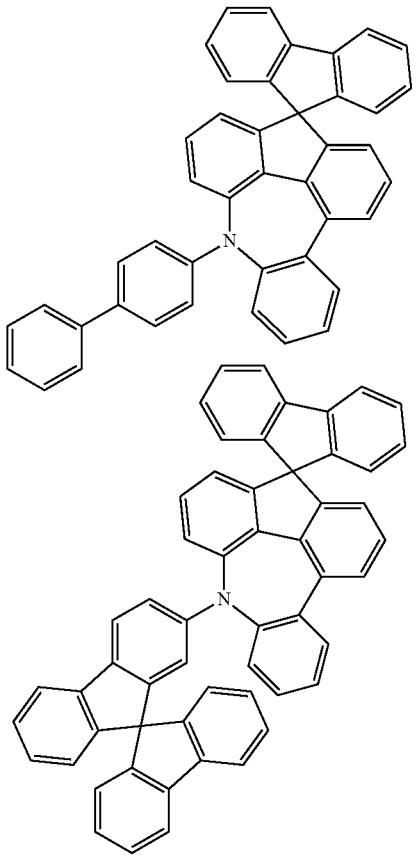

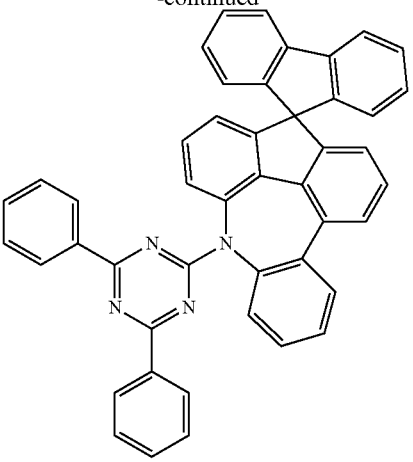

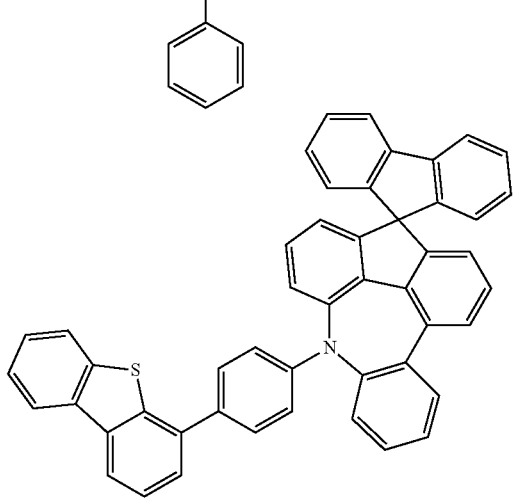

In another aspect, an organic layer comprises a host material with a spirobisfluorene compound having hole transfer properties bonded to a material having electron transfer properties to optimize the lifetime and efficiency of an organic light emitting display device.

The material with electron transfer properties includes a heteroaryl group.

The organic layer includes a compound represented by the following Chemical Formula 1:

[Chemical Formula 1]

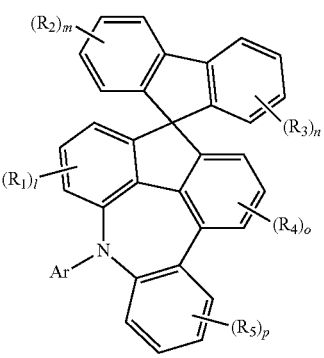

where R₁ to R₅ are independently one among hydrogen, deuterium, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l and o are an integer between 0 and 3, and m, n, and p are an integer between 0 and 4, wherein, if any of l, m, n, o, and p has a value of 2 or more, the corresponding R is the same with each other or if any of l, m, n, o, and p has a value of 2 or more, the corresponding R is different from each other, and Ar is a substituted or unsubstituted aryl group having 6 to 30 carbon atoms or a substituted or unsubstituted heteroaryl group having 2 to 30 carbon atoms.

The compound includes one among the following compounds:

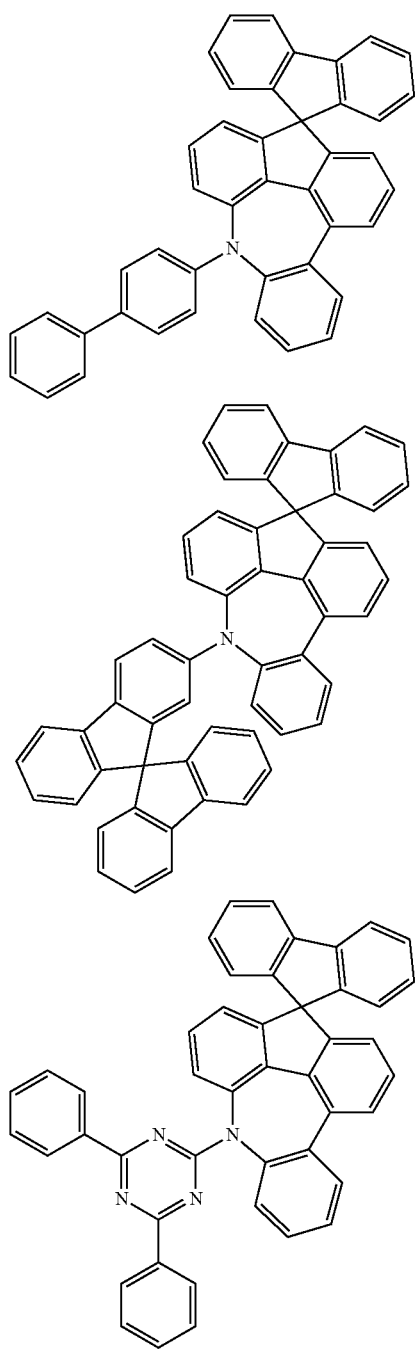

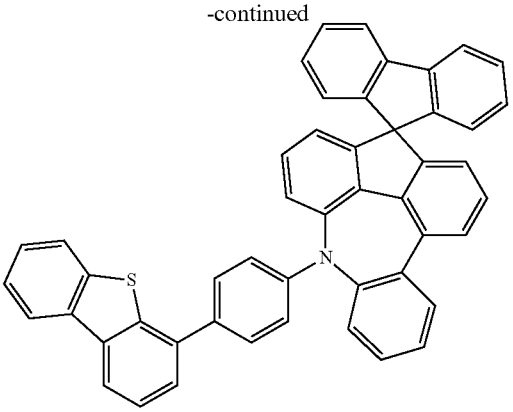

The triplet energy of the host material is equal to or greater than 2.5 eV.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

Figure 1:
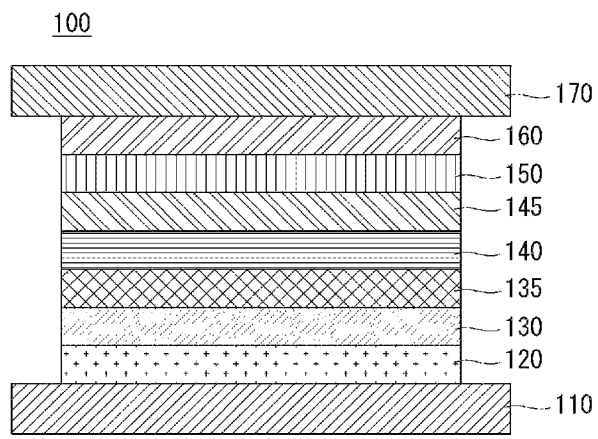
FIG. 1 is a view showing an organic light emitting display device according to an example embodiment of the present invention.

The advantages and features of the present invention and methods for accomplishing the same may be understood more readily by reference to the following detailed descriptions of exemplary embodiments and the accompanying drawings. The present invention may, however, be embodied in many different forms and should not be construed as being limited to the exemplary embodiments set forth herein. Rather, these exemplary embodiments are provided so that this disclosure will be thorough and complete and will fully convey the concept of the present invention to those skilled in the art, and the present invention is defined by the appended claims The shapes, sizes, percentages, angles, numbers, etc shown in the figures to describe the exemplary embodiments of the present invention are merely examples and not limited to those shown in the figures. Like reference numerals denote like elements throughout the specification. In describing the present invention, detailed descriptions of related well-known technologies will be omitted to avoid unnecessary obscuring the present invention. When the terms 'comprise', 'have', 'consist of' and the like are used, other parts may be added as long as the term 'only' is not used. The singular forms may be interpreted as the plural forms unless explicitly stated.

The elements may be interpreted to include an error margin even if not explicitly stated.

When the position relation between two parts is described using the terms 'on', 'over', 'under', 'next to' and the like, one or more parts may be positioned between the two parts as long as the term 'immediately' or 'directly' is not used.

When the temporal relationship between two events is described using the terms 'after', 'following', 'next', 'before' and the like, the two events may not occur in succession as long as the term 'immediately' or 'directly' is not used.

It will be understood that, although the terms first, second, etc., may be used to describe various elements, these elements should not be limited by these terms. These terms are only used to distinguish one element from another element. Thus, a first element discussed below could be termed a second element without departing from the technical spirit of the present invention.

The features of various exemplary embodiments of the present invention may be combined with one another either partly or wholly, and may technically interact or work together in various ways. The exemplary embodiments may be carried out independently or in combination with one another.

Hereinafter, various exemplary embodiments of the present invention will be described in detail with reference to the accompanying drawings.

FIG. 1 is a view showing an organic light emitting display device according to an example embodiment of the present invention.

With reference to FIG. 1, an organic light emitting display device 100 according to an example embodiment of the present invention comprises organic layers 120, 130, 135, 140, 145, 150, and 160 between an anode 110 and a cathode 170. The anode 110 is a hole injection electrode, and may be formed of either ITO (indium tin oxide), IZO (indium zinc oxide), or ZnO (zinc oxide) having a high work function. Also, if the anode 110 is a reflective electrode, the anode 110 may further comprise a reflective layer formed of aluminum (Al), silver (Ag), or nickel (Ni) under a layer formed of ITO, IZO, or ZnO.

A hole injection layer 120 is over the anode 110. The hole injection layer 120 may function to facilitate hole injection from the anode 110 to a light emitting layer 140, and may be formed of, but are not limited to, one among CuPc (copper phthalocyanine), PEDOT (poly(3,4)-ethylenedioxythiophene), PANI (polyaniline), and NPD ((N,N'-bis(naphthalene-1-yl)-N,N'-bis(phenyl)-2,2'-dimethylbenzidine). The hole injection layer 120 may be 1 to 150 nm thickness. If the hole injection layer 120 is 1 nm thickness or greater, the hole injection properties may be improved, or if the hole injection layer 120 is 150 nm thickness or less, an increase in the thickness of the hole injection layer 120 may be prevented and a rise in operating voltage may be therefore prevented.

The hole injection layer 120 may not be included in the composition of the organic light emitting display device, depending on the structure or characteristics of the device.

A hole transport layer 130 is over the hole injection layer 120. The hole transport layer 130 may function to facilitate hole transport, and may be formed of, but are not limited to, one among NPD (N,N'-bis(naphthalene-1-yl)-N,N'-bis(phenyl)-2,2'-dimethylbenzidine), TPD (N,N'-bis-(3-methylphenyl)-N,N'-bis(phenyl)-benzidine), spiro-TAD (2,2'7,7'-tetrakis(N,N-diphenylamino)-9,9'-spirofluorene), and MTDATA (4,4',4"-Tris(N-3-methylphenyl-N-phenylamino)-triphenylamine). The hole transport layer 130 may be 1 to 150 nm thickness. If the hole transport layer 130 is 1 nm thickness or greater, the hole transport properties may be improved, or if the hole transport layer 130 is 150 nm thickness or less, an increase in the thickness of the hole transport layer 130 may be prevented, and a rise in operating voltage may be therefore prevented.

An electron blocking layer 135 is over the hole transport layer 130. The electron blocking layer 135 functions to block electrons injected from the cathode 170 from moving to the anode 110, and may be formed of, but are not limited to, one among TPD (N,N'-bis-(3-methylphenyl)-N,N'-bis (phenyl)-benzidine), NPD (N,N'-bis(naphthalene-1-yl)-N, N'-bis(phenyl)-2,2'-dimethylbenzidine), TCTA (4,4'4"-tris) carbozoyl-9-yl)triphenylamine), and CBP (4,4'-bis (carbazol-9-yl)biphenyl. The electron blocking layer 135 may not be included in the composition of the organic light emitting display device, depending on the structure or characteristics of the device.

The light emitting layer 140 is over the electron blocking layer 135. The light emitting layer 140 may emit light of red (R), green (G), and blue (B), and may be formed of a phosphorescent material. The light emitting layer 140 comprises a host and a dopant. The host serves to transfer energy to the dopant. Thus, the present inventors used a heterocyclic compound as the host, in order to improve the properties of the light emitting layer 140.

The heterocyclic compound is capable of improving the efficiency and lifetime of the device because its rigid structure with hetero rings bridged together allows the energy of thermal motion of the host to be consumed only for light emission but not for other things. Moreover, a heterocyclic compound having spirobisfluorene and heteroaryl has high triplet energy and achieves thermal stability. In addition, the use of a heterocyclic compound as at least one among the following: the hole transport layer, the electron blocking layer, the hole blocking layer, and the electron transport layer can facilitate hole or electron injection into the light emitting layer, thereby improving the lifetime of the organic light emitting display device. And the light emitting layer with phosphorescent material includes the heterocyclic compound. Even though the heterocyclic compound has high triplet energy, the heterocyclic compound may be applied the light emitting layer with the phosphorescent material without decreasing the lifetime and efficiency of the organic light emitting display device. The light emitting layer with phosphorescent material includes yellow-green light emitting layer or green light emitting layer.

The heterocyclic compound has spirobisfluorene with hole transfer properties and heteroaryl with electron or hole transfer properties. Especially, the heterocyclic compound has bipolarity involving the properties of both holes and electrons by having spirobisfluorene with hole transfer properties and heteroaryl with electron transfer properties, and therefore has electric stability against holes and electrons. Also, a host material with a spirobisfluorene compound with hole transfer properties bound to a material with electron transfer properties may be used to optimize the lifetime and efficiency of an organic light emitting layer. The material with electron transfer properties may have a heteroaryl group. Thus, the use of a heterocyclic compound with electric stability against holes and electrons as a host for the light emitting layer can increase the light emission area of the light emitting layer and therefore improve the lifetime of the device.

Accordingly, a host for the light emitting layer 140 of the present invention includes a heterocyclic compound represented by the following Chemical Formula 1:

[Chemical Formula 1]

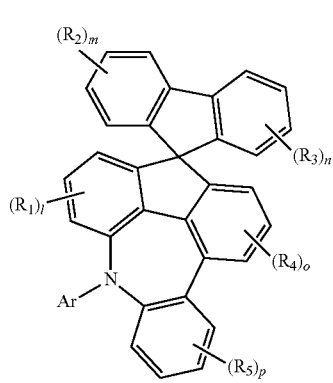

where $R_1$ to $R_5$ are independently one among hydrogen, deuterium, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l and o are an integer between 0 and 3, and m, n, and p are an integer between 0 and 4. If any of l, m, n, o, and p has a value of 2 or more, the corresponding R is the same with each other or any of l, m, n, o, and p has a value of 2 or more, the corresponding R is different from each other. Ar is a substituted or unsubstituted aryl group having 6 to 30 carbon atoms or a substituted or unsubstituted heteroaryl group having 2 to 30 carbon atoms.

If $R_1$ to $R_5$ are independently one among a substituted alkyl group, a substituted aryl group, a substituted heteroaryl group, a substituted aryl amino group, and a substituted heteroaryl amino group, substituents are independently one among a methyl group, an ethyl group, a n-propyl group, an isopropyl group, a sec-propyl group, a n-butyl group, a sec-butyl group, an isobutyl group, a tert-butyl group, a phenyl group, an o-tolyl group, a m-tolyl group, a p-tolyl group, a xylyl group, a terphenyl group, a naphthyl group, a phenanthrolyl group, a fluorenyl group, 9,9-dimethylfluorenyl group, 9,9-diphenylfluorenyl group, a triphenylenyl group, a pyrrole group, a furyl group, a thiophenyl group, an imidazolyl group, a carbazolyl group, a dibenzo furyl group, a dibenzothiophenyl group, a halogen group, and a cyano group.

The heterocyclic compound includes one among the following compounds:

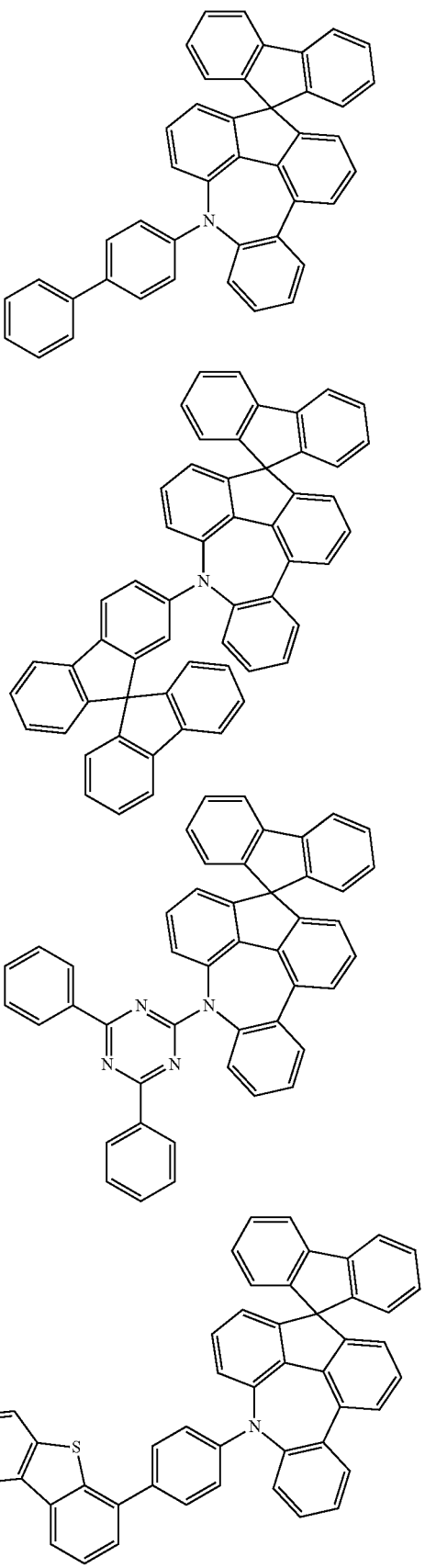

If the light emitting layer 140 is a red emitting layer, it may be formed of, but are not limited to, a phosphorescent material comprising a dopant having one or more among Ir(PIQ)$_2$(acac)(bis(1-phenylisoquinoline) acetylacetonate iridium(M)), Ir(PIQ)$_3$(tris(1-phenylquinoline)iridium(M)), and PtOEP(octaethylporphine platinum). If the light emitting layer 140 is a green emitting layer, it may be formed of, but are not limited to, a phosphorescent material comprising a host material such as CBP (4,4'-bis(carbazole-9-yl)biphenyl) and a dopant material comprising an iridium-based material. Alternatively, the light emitting layer 140 may be formed of, but are not limited to, a fluorescent material comprising Alq$_3$(tris(8-hydroxyquinolinato)aluminum). If the light emitting layer 140 is a blue emitting layer, it may be formed of, but are not limited to, a phosphorescent material comprising a host material such as CBP (4,4'-bis(carbazole-9-yl)biphenyl) and a dopant material comprising an iridium-based material. Alternatively, the light emitting layer 140 may be formed of, but are not limited to, a fluorescent material comprising any one among spiro-DPVBi, spiro-CBP, distyrylbenzene (DSB), distyrylarylene (DSA), a PFO polymer, and a PPV polymer.

A hole blocking layer 145 is over the light emitting layer 140. The hole blocking layer 145 functions to block holes injected from the anode 110 from moving to the cathode 170, and may be formed of, but are not limited to, one among BAlq (Bis(2-methyl-8-quinolinolate)-4-(phenylphenolato)aluminum), BCP (2,9-dimethyl-4,7-diphenyl-1,10-phenanthroline), and TPBI (2,2'2"-(1,3,5-benzinetriyl)-tris(1-phenyl-1-H-benzimidazole). The hole blocking layer 145 is 10 to 100 Å thickness. This is because, if the hole blocking layer 145 is less than 10 Å thickness, it has poor hole blocking properties, or if the hole blocking layer 145 is more than 100 Å thickness, the operating voltage of the device may rise. The hole blocking layer 145 may not be included in the composition of the organic light emitting display device, depending on the structure or characteristics of the device.

An electron transport layer 150 is over the hole blocking layer 145. The electron transport layer 150 functions to facilitate electron transport, and may be formed of, but are not limited to, one or more among Alq$_3$(tris(8-hydroxyquinolinato)aluminum), PBD (2-(4-biphenyl)-5-(4-tert-butylphenyl)-1,3,4-oxadiazole), TAZ (3-(4-biphenyl)-4-pheynyl-5-tert-butylphenyl-1,2,4-triazole), and BAlq (Bis(2-methyl-8-quinolinolate)-4-(phenylphenolato)aluminum). The electron transport layer 150 may be 1 to 150 nm thickness. If the electron transport layer 150 is 1 nm thickness or greater, a degradation of the electron transport properties may be prevented, or if the electron transport layer 150 is 150 nm thickness or less, an increase in the thickness of the electron transport layer 150 may be prevented, and a rise in operating voltage may be therefore prevented.

An electron injection layer 160 is over the electron transport layer 150. The electron injection layer 160 functions to facilitate electron injection, and may be formed of, but are not limited to, one among Alq$_3$ (tris(8-hydroxyquinolinato)aluminum), PBD (2-4-biphenyl)-5-(4-tert-butylphenyl)-1,3,4-oxadiazole), TAZ (3-(4-biphenyl)-4-pheynyl-5-tert-butylphenyl-1,2,4-triazole), or BAlq (Bis(2-methyl-8-quinolinolate)-4-(phenylphenolato)aluminum). On the other hand, the electron injection layer 160 may be formed of a metal compound, and the metal compound may be, for example, but are not limited to, one among LiQ, LiF, NaF, KF, RbF, CsF, FrF, BeF$_2$, MgF$_2$, CaF$_2$, SrF$_2$, BaF$_2$, and RaF$_2$. The electron injection layer 160 may be 1 to 50 nm thickness. If the electron injection layer 160 is 1 nm thickness or greater, a degradation of the electron injection properties may be prevented, or if the electron injection layer 160 is 50 nm thickness or less, an increase in the thickness of the electron injection layer 160 may be prevented, and a rise in operating voltage may be therefore prevented.

The cathode 170 is an electron injection electrode, and may be formed of magnesium (Mg), calcium (Ca), aluminum (Al), silver (Ag), or an alloy thereof, having a low work function. If the organic light emitting display device is a top-emission type or a dual-emission type, the cathode 170 may be formed thin enough to pass light therethrough. If the organic light emitting display device is a bottom-emission type, the cathode 170 may be formed thick enough to reflect light.

As stated above, the heterocyclic compound is capable of improving the efficiency and lifetime of the device because its rigid structure with hetero rings bridged together allows the energy of thermal motion of the host to be consumed only for light emission but not for other things. Moreover, a heterocyclic compound having spirobisfluorene and heteroaryl has high triplet energy and achieves thermal stability.

The heterocyclic compound has spirobisfluorene with hole transfer properties and heteroaryl with hole or electron transfer properties. Especially, the heterocyclic compound has bipolarity involving the properties of both holes and electrons by having spirobisfluorene with hole transfer properties and and heteroaryl with electron transfer properties, and therefore has electric stability against holes and electrons. Also, a host material with a spirobisfluorene compound with hole transfer properties bound to a material with electron transfer properties may be used to optimize the lifetime and efficiency of an organic light emitting layer. The material with electron transfer properties may include a heteroaryl group. Thus, the use of a heterocyclic compound with electric stability against holes and electrons as a host for the light emitting layer can increase the light emission area of the light emitting layer and therefore improve the lifetime of the device. And, the host of the light emitting layer with phosphorescent material includes the heterocyclic compound. Even though the heterocyclic compound has high triplet energy, the heterocyclic compound may be applied the light emitting layer with the phosphorescent material without decreasing the lifetime and efficiency of the organic light emitting display device. The light emitting layer with phosphorescent material includes yellow-green light emitting layer or green light emitting layer.

The exemplary embodiment includes one light emitting part, but is not limited thereto. The present invention includes at least two light emitting parts. The at least two light emitting parts includes a first light emitting part and a second light emitting part. The first light emitting part includes a first light emitting layer, a first hole transport layer and a first electron transport layer. The first light emitting layer includes one among a blue light emitting layer, a deep blue light emitting layer or a sky blue emitting layer. The first hole transport layer and the first electron transport layer may be formed of the hole transport layer and the electron transport layer as described above, but are not limited thereto. And the second light emitting part on the first light emitting part includes a second light emitting layer, a second hole transport layer and a second electron transport layer. The second light emitting layer includes yellow-green light emitting layer or a green emitting layer. The second hole transport layer and the second electron transport layer may be formed of the hole transport layer and the electron transport layer as described above, but are not limited thereto. A charge generation layer further includes between the first light emitting part and the second light emitting part. The charge generation layer generates a charge, or injects the charge, i.e., electrons and holes, separately into the first and second light emitting layers. And the at least two light emitting parts further includes a third light emitting part on the second light emitting part. The third light emitting part includes a third light emitting layer, a third hole transport layer and a third electron transport layer. The third light emitting layer includes one among a blue light emitting layer, a deep blue light emitting layer or a sky blue emitting layer. The third hole transport layer and the third electron transport layer may be formed of the hole transport layer and the electron transport layer as described above, but are not limited thereto. Another charge generation layer further includes between the second light emitting part and the third light emitting part. Another charge generation layer generates a charge, or injects the charge, i.e., electrons and holes, separately into the second and third light emitting layers. Hereinafter, synthesis examples of heterocyclic compounds of the present invention and the properties of these compounds will be described in detail. However, the following examples are only for illustration, and the present invention is not limited thereto.

Synthesis of Compound A

1) Synthesis of Compound A-1

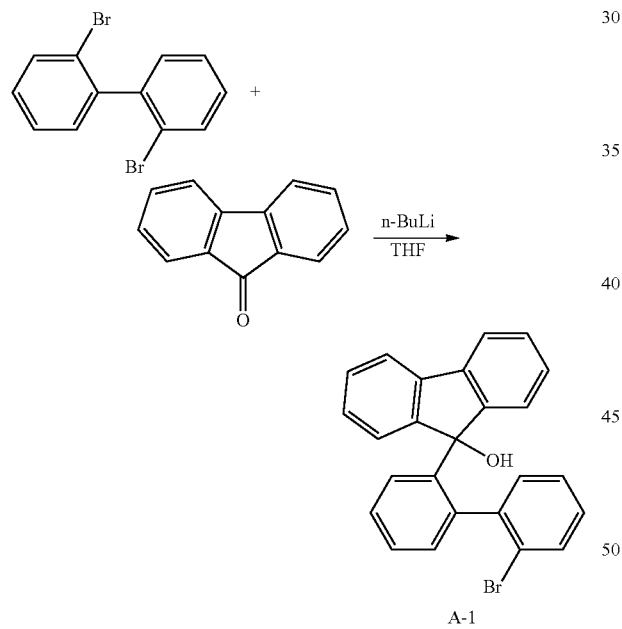

A-1

1-1'-dibromobiphenyl (50.0 g, 0.16 mol) was put into a 2 L round bottom flask and dissolved in 500 mL of tetrahydrofurane (THF), and cooled at −78° C. 2.5M n-BuLi (64.1 mL, 0.16 mol) was dropped to the mixture and stirred for 2 hours, and then 34.7 g of 9H-fluoren-9-one dissolved in 200 mL of tetrahydrofuran (THF) was dropped to the mixture. After the dropping, the temperature was gradually raised to room temperature, and the mixture was stirred for 12 hours, whereby organic layers were obtained by extraction with ethyl acetate and water. The organic layers were combined and distilled under reduced pressure to remove the solvent and the volatile by-products, and the residue was used for the subsequent reaction without further purification.

2) Synthesis of Compound A-2

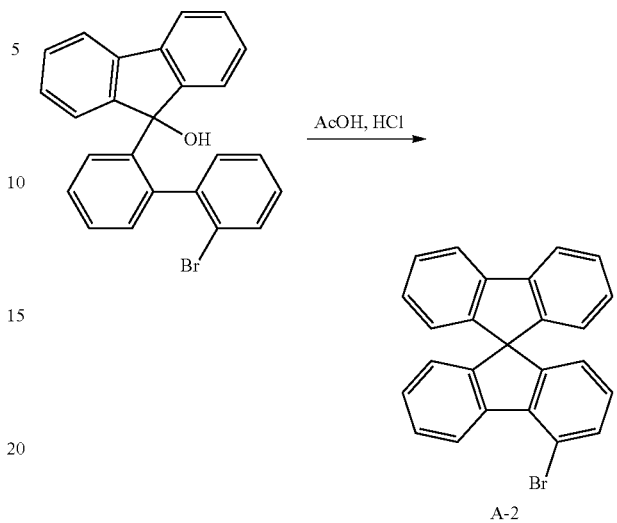

A-2

60 g of the unpurified Compound A-1 obtained above was put into a 1 L round bottom flask, followed by the addition of 600 mL of $CH_3COOH$ and 60 mL of 36% HCl, and the mixture was refluxed and stirred for 12 hours. After completion of the reaction, the solution was cooled down, and the resulting solid was filtered off. The filtered solid was washed three times with methanol ($CH_3OH$), and Compound A-2 was obtained from the residue solid through column chromatography.

3) Synthesis of Compound A-3

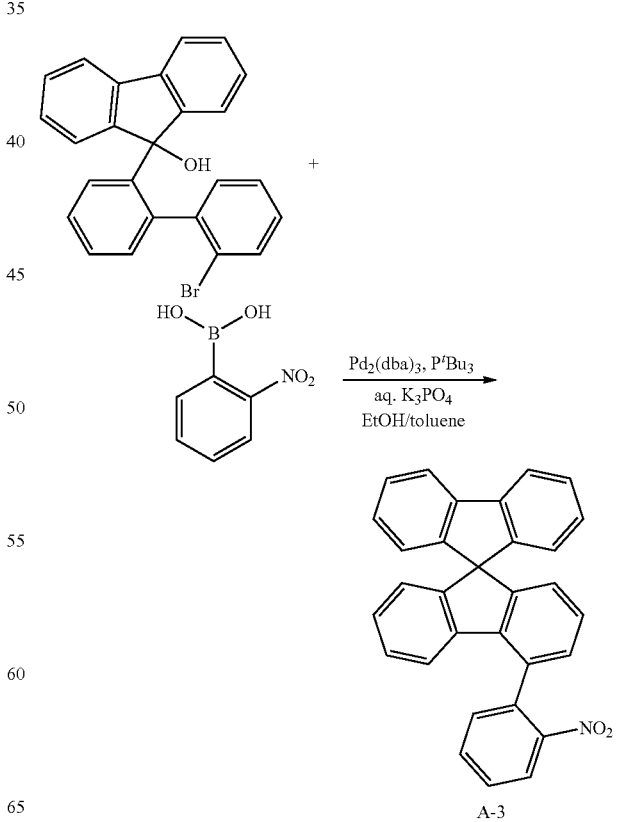

A-3

Compound A-2 (30.0 g, 75.9 mmol), 2-nitrophenylboronic acid (15.2 g, 91.1 mmol), Pd$_2$(dba)$_3$ (tris(dibenzylideneacetone)dipalladium(0) (3.47 g, 3.8 mmol), P$^t$Bu$_3$ (1.84 g, 9.1 mmol), 80 mL of 1.3M potassium phosphate (K$_3$PO$_4$) aqueous solution, 150 mL of ethanol, and 600 mL of toluene were put into a 1 L round bottom flask, and then refluxed and stirred. After confirming completion of the reaction through TLC, organic layers were obtained from the reaction solution by extraction with dichloromethane (CH$_2$Cl$_2$) and water, and the organic layers were distilled under reduced pressure and then subjected to column chromatography using dichloromethane (CH$_2$Cl$_2$) and n-hexane (in a volume ratio of 1:3), thereby obtaining Compound A-3.

4) Synthesis of Compound A-4

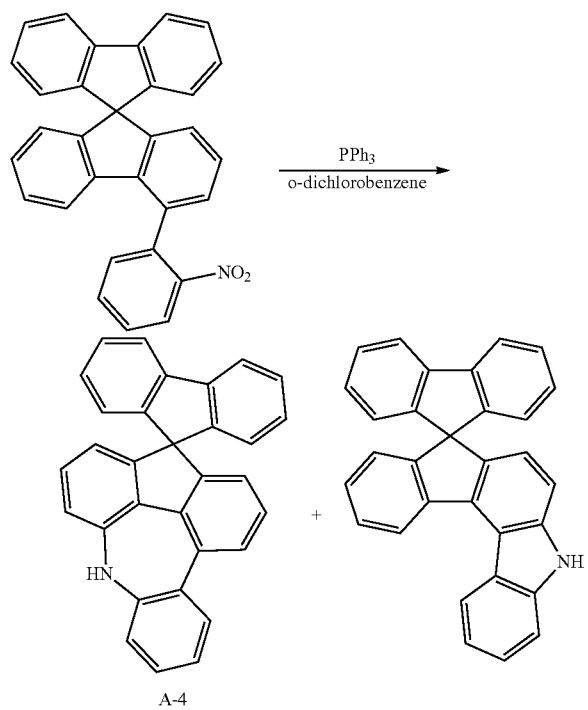

A-4

Compound A-3 (40.0 g, 91.4 mmol), PPh$_3$ (triphenylphosphine) (71.9 g, 274 mmol), and 400 mL of o-dichlorobenzene were put into a 1 L round bottom flask, and the mixture was refluxed and stirred for 2 days. After completion of the reaction, the reaction solution was distilled under reduced pressure to remove the volatile by-products, and then subjected to column chromatography using dichloromethane (CH$_2$Cl$_2$) and n-hexane (in a volume ratio of 1:5), thereby obtaining Compound A-4.

5) Synthesis of Compound A

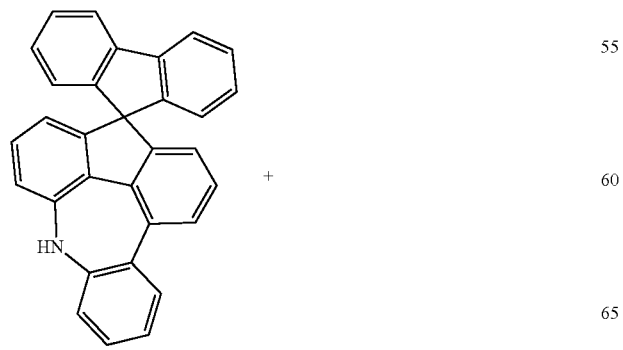

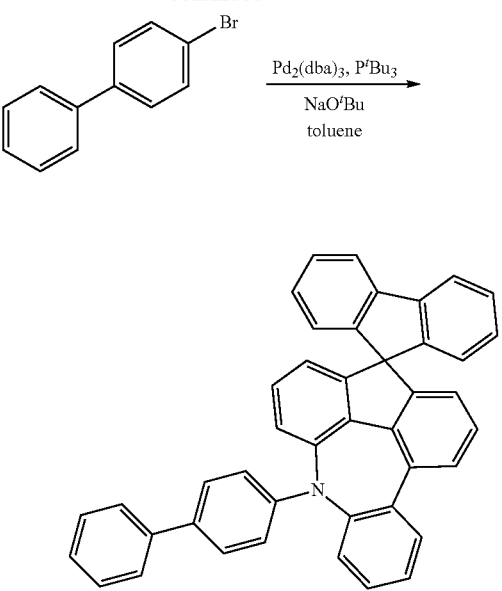

A

Compound A-4 (6.0 g, 14.8 mmol), 4-bromobiphenyl (4.2 g, 17.8 mmol), Pd$_2$(dba)$_3$ (tris(dibenzylideneacetone)dipalladium(0) (0.68 g, 0.74 mmol), P$^t$Bu$_3$ (0.36 g, 1.78 mmol), NaOtBu (3.2 g, 33.3 mmol), and 120 mL of toluene were put into a 250 mL round bottom flask under an argon atmosphere, and the mixture was refluxed and stirred. Organic layers were obtained from the reaction solution by extraction with dichloromethane (CH$_2$Cl$_2$) and water, and the organic layers were distilled under reduced pressure and then subjected to column chromatography using dichloromethane (CH$_2$Cl$_2$) and n-hexane (in a volume ratio of 1:4), thereby obtaining Compound A.

Synthesis of Compound B

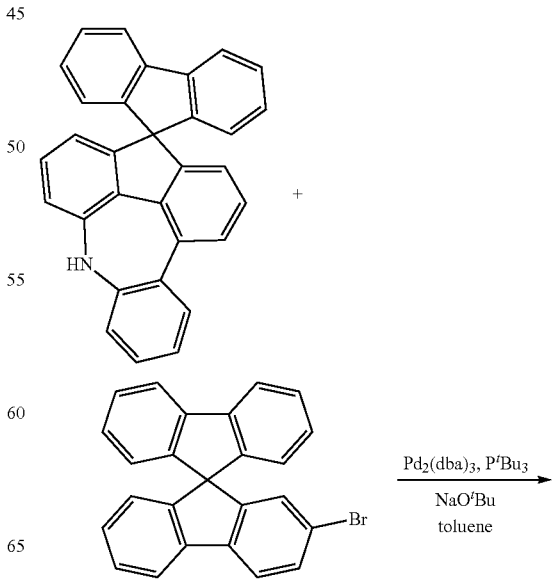

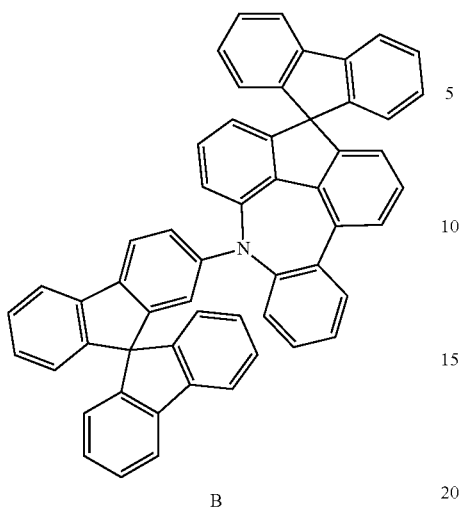

B

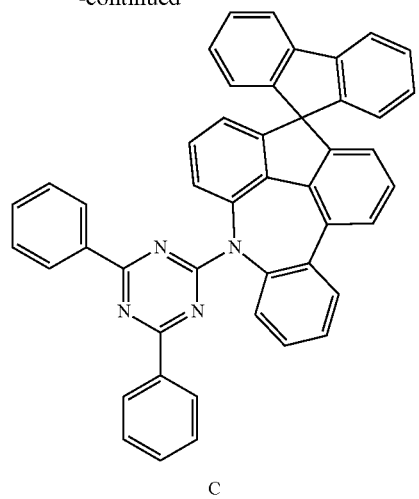

C

Compound A-4 (6.0 g, 14.8 mmol), 4-bromobiphenyl (10.2 g, 17.8 mmol), Pd$_2$(dba)$_3$ (tris(dibenzylideneacetone)dipalladium(0) (0.68 g, 0.74 mmol), PtBu$_3$ (0.36 g, 1.78 mmol), NaOtBu (3.2 g, 33.3 mmol), and 120 mL of toluene were put into a 250 mL round bottom flask under an argon atmosphere, and the mixture was refluxed and stirred. Organic layers were obtained from the reaction solution by extraction with dichloromethane (CH$_2$Cl$_2$) and water, and the organic layers were distilled under reduced pressure and then subjected to column chromatography using dichloromethane (CH$_2$Cl$_2$) and n-hexane (in a volume ratio of 1:5), thereby obtaining Compound B.

Synthesis of Compound C.

Compound A-4 (6.0 g, 14.8 mmol), 2-chloro-diphenyl-1,3,5-triazine (4.8 g, 17.8 mmol), Pd$_2$(dba)$_3$ (tris(dibenzylideneacetone)dipalladium(0) (0.68 g, 0.74 mmol), PtBu$_3$ (0.36 g, 1.78 mmol), NaOtBu (3.2 g, 33.3 mmol), and 120 mL of toluene were put into a 250 mL round bottom flask under an argon atmosphere, and the mixture was refluxed and stirred. Organic layers were obtained from the reaction solution by extraction with dichloromethane (CH$_2$Cl$_2$) and water, and the organic layers were distilled under reduced pressure and then subjected to column chromatography using dichloromethane (CH$_2$Cl$_2$) and n-hexane (in a volume ratio of 1:3), thereby obtaining Compound C.

Synthesis of Compound D

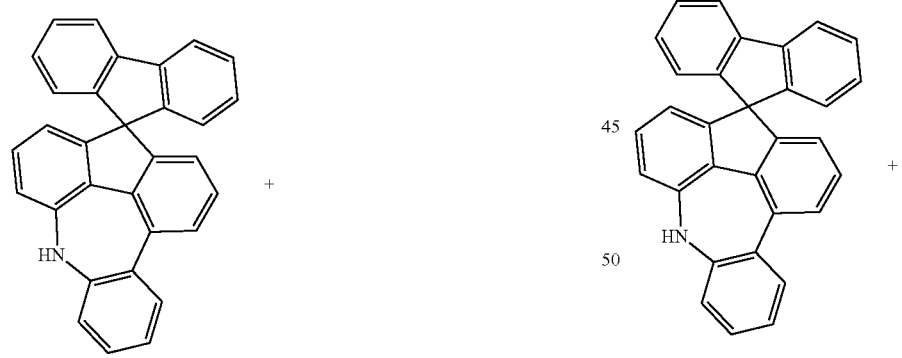

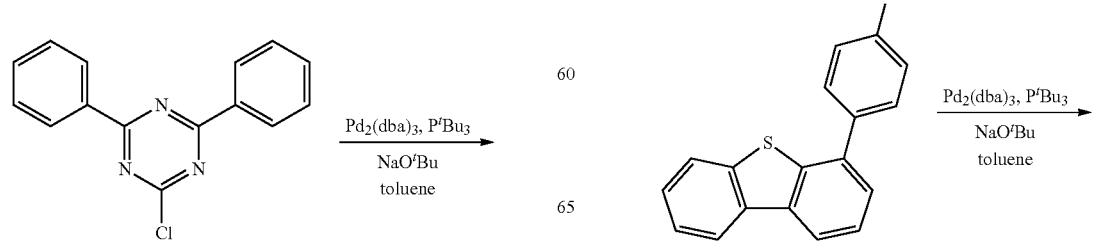

-continued

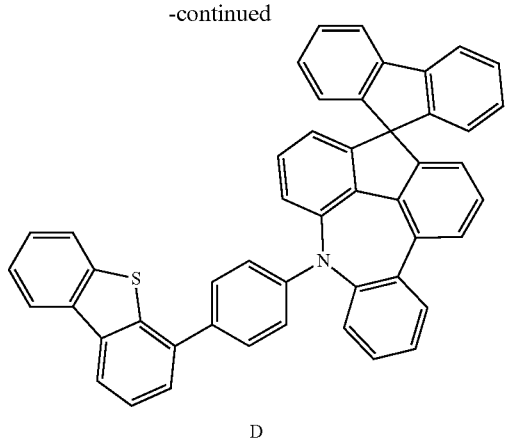

D

Compound A-4 (6.0 g, 14.8 mmol), 4-bromobiphenyl (6.0 g, 17.8 mmol), Pd$_2$(dba)$_3$ (tris(dibenzylideneacetone)dipalladium(0) (0.68 g, 0.74 mmol), PtBu$_3$ (0.36 g, 1.78 mmol), NaOtBu (3.2 g, 33.3 mmol), and 120 mL of toluene were put into a 250 mL round bottom flask under an argon atmosphere, and the mixture was refluxed and stirred. Organic layers were obtained from the reaction solution by extraction with dichloromethane (CH$_2$Cl$_2$) and water, and the organic layers were distilled under reduced pressure and then subjected to column chromatography using dichloromethane (CH$_2$Cl$_2$) and n-hexane (in a volume ratio of 1:4), thereby obtaining Compound D.

Figure 2:
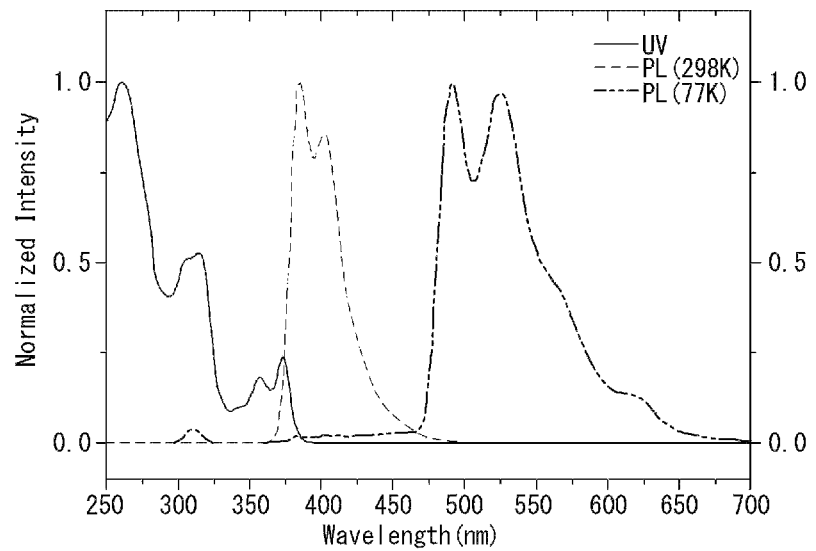
FIG. 2 is a graph showing the UV absorption spectrum, PL spectrum, and low-temperature (−77K) PL spectrum of Compound A according to an example embodiment of the present invention.
Figure 3:
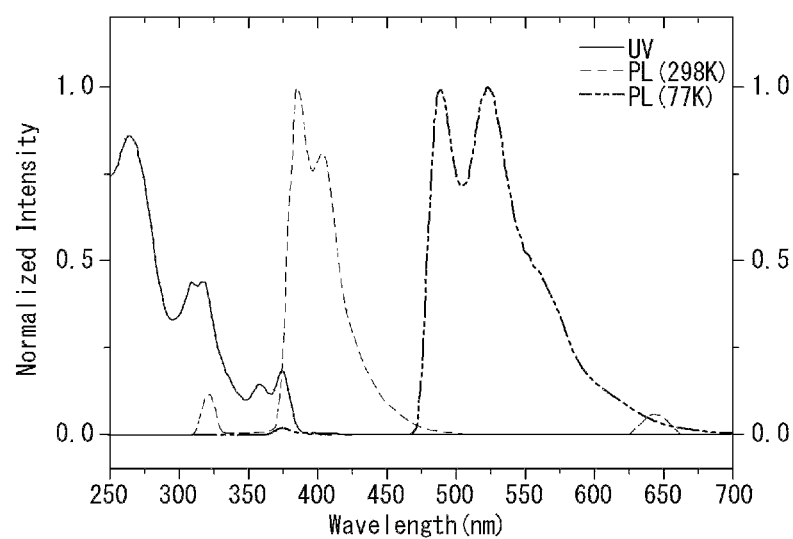
FIG. 3 is a graph showing the UV absorption spectrum, PL spectrum, and low-temperature (−77K) PL spectrum of Compound B according to an example embodiment of the present invention.
Figure 4:
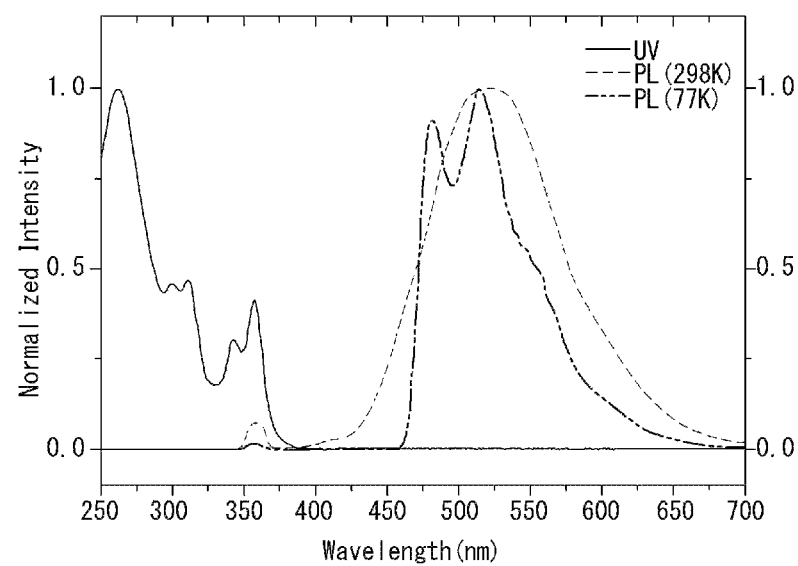
FIG. 4 is a graph showing the UV absorption spectrum, PL spectrum, and low-temperature (−77K) PL spectrum of Compound C according to an example embodiment of the present invention.
Figure 5:
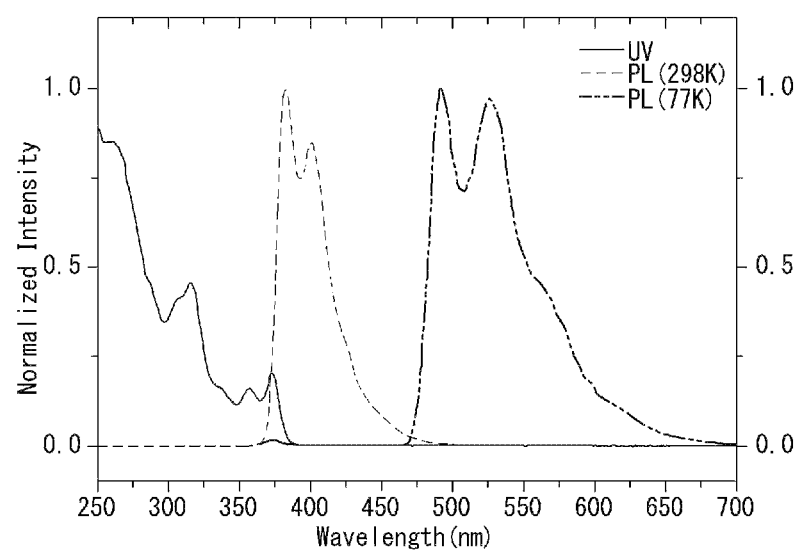
FIG. 5 is a graph showing the UV absorption spectrum, PL spectrum, and low-temperature (−77K) PL spectrum of Compound D according to an example embodiment of the present invention.

The UV absorption spectrum, PL spectrum, and low-temperature (−77K) PL spectrum of Compound A were measured and shown in FIG. 2, the UV absorption spectrum, PL spectrum, and low-temperature (−77K) PL spectrum of Compound B were measured and shown in FIG. 3, the UV absorption spectrum, PL spectrum, and low-temperature (−77K) PL spectrum of Compound C were measured and shown in FIG. 4, and the UV absorption spectrum, PL spectrum, and low-temperature (−77K) PL spectrum of Compound D were measured and shown in FIG. 5. A UV spectrum refers to the absorption spectrum of a material irradiated with light in the UV region, a PL spectrum refers to the spectrum of a material produced when an excited electron drops to the ground state, and a low-temperature PL spectrum refers to the PL spectrum of a material at a low temperature, in which the first peak in a longer wavelength region than in the room-temperature PL spectrum represents the triplet energy. In FIGS. 2 to 5, the maximum intensity of light in the UV absorption spectrum was set to 1.0, and the PL and low-temperature PL spectrum measurements were shown to be proportional to the UV absorption spectrum measurements.

With reference to FIG. 2, Compound A showed a wavelength of 262 nm at the peak value of the UV absorption spectrum, a wavelength of 383 nm at the peak value of the PL spectrum, and a wavelength of 490 nm at the peak value of the low-temperature PL spectrum. Also, it was found out from the low-temperature PL spectrum that the triplet energy was 2.53 eV, so Compound A of the present invention may be suitable as a host.

With reference to FIG. 3, Compound B showed a wavelength of 262 nm at the peak value of the UV absorption spectrum, a wavelength of 383 nm at the peak value of the PL spectrum, and a wavelength of 489 nm at the peak value of the low-temperature PL spectrum. Also, it was found out from the low-temperature PL spectrum that the triplet energy was 2.53 eV, so Compound B of the present invention may be suitable as a host.

With reference to FIG. 4, Compound C showed a wavelength of 262 nm at the peak value of the UV absorption spectrum, a wavelength of 520 nm at the peak value of the PL spectrum, and a wavelength of 480 nm at the peak value of the low-temperature PL spectrum. Also, it was found out from the low-temperature PL spectrum that the triplet energy was 2.58 eV, so Compound C of the present invention may be suitable as a host.

With reference to FIG. 5, Compound D showed a wavelength of 381 nm at the peak value of the PL spectrum and a wavelength of 483 nm at the peak value of the low-temperature PL spectrum. Also, it was found out from the low-temperature PL spectrum that the triplet energy is 2.56 eV, so Compound D of the present invention may be suitable as a host.

Thus, it can be seen that compounds of the present invention can be used as a host for the light emitting layer. Also, it can be seen that the triplet energy of a compound used as the host is equal to or greater than 2.5 eV. As such, energy transfer from a dopant to the host is facilitated, and the compound, even with the high triplet energy, offers superior thermal stability and superior electric stability without a decrease in device's lifetime.

Hereinafter, an embodiment for the manufacture of an organic light emitting display device according to the present invention will be disclosed. However, the following materials for the electron transport layer do not limit the scope of the present invention.

COMPARATIVE EXAMPLE

An organic light emitting display device was manufactured by forming, on a substrate, a hole injection layer, a hole transport layer, an electron blocking layer, a light emitting layer, a hole blocking layer, an electron transport layer, an electron injection layer, and a cathode. The light emitting layer was a green light emitting layer which comprises CBP as a host and Ir(Ppy)$_3$ with a 15% doping concentration. The device used in testing was a mono device.

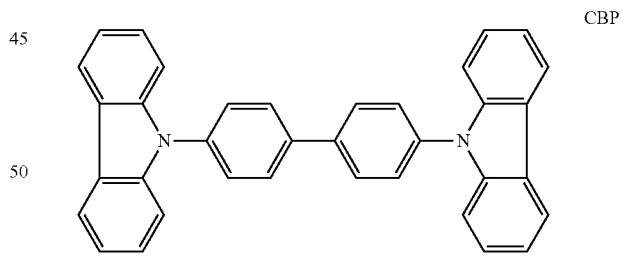

CBP

Embodiment 1

The organic light emitting display device has the same composition as Comparative Example, and the light emitting layer is a green light emitting layer which comprises Compound A as a host and Ir(ppy)$_3$ as a dopant with a 15% doping concentration.

Embodiment 2

The organic light emitting device has the same composition as Comparative Example, and the light emitting layer is a green light emitting layer which comprises Compound B as a host and Ir(ppy)₃ as a dopant with a 15% doping concentration.

Embodiment 3

The organic light emitting device has the same composition as Comparative Example, and the light emitting layer is a green light emitting layer which comprises Compound D as a host and Ir(ppy)₃ as a dopant with a 15% doping concentration.

The materials for the light emitting layer used in the above Comparative Example and Embodiments 1 to 3 do not limit the scope of the present invention.

The operating voltage, current density, external quantum efficiency, and lifetime of the devices manufactured according to Comparative Example and Embodiments 1 to 3 were measured and shown in the following Table 1. The measurements taken in Embodiments 1 to 3 were expressed as a percentage relative to those taken in Comparative Example corresponding to 100%, and the devices manufactured according to Comparative Example and Embodiments 1 to 3 were driven at an operating current of 10 mA/cm.

TABLE 1

|  | Operating voltage (%) | External quantum efficiency (%) | Lifetime (%) |
| --- | --- | --- | --- |
| Comparative Example | 100 | 100 | 100 |
| Embodiment 1 | 84 | 113 | 390 |
| Embodiment 2 | 91 | 106 | 461 |
| Embodiment 3 | 87 | 121 | 498 |

With reference to Table 1, Embodiment 1 using the heterocyclic compound A as a host for the light emitting layer showed a 16% decrease in operating voltage, a 13% increase in external quantum efficiency, and a 390% increase in lifetime, compared to Comparative Example using CBP as a host for the light emitting layer. Embodiment 2 using the heterocyclic compound B as a host for the light emitting layer showed a 9% decrease in operating voltage, a 6% increase in external quantum efficiency, and a 461% increase in lifetime, compared to Comparative Example. Embodiment 3 using the heterocyclic compound D as a host for the light emitting layer showed a 13% decrease in operating voltage, a 21% increase in external quantum efficiency, and a 498% increase in lifetime, compared to Comparative Example.

From these results, it can be found out that a decrease in operating voltage and an increase in lifetime and external quantum efficiency can be achieved by using heterocyclic compounds as a host for the light emitting layer. Accordingly, it can be seen that an organic light emitting display device having a compound of the present invention has higher triplet energy, reduced operating voltage, and improved lifetime, as compared with an organic light emitting display device without this compound.

As seen from above, a heterocyclic compound of the present invention is capable of improving the efficiency and lifetime of the device because its rigid structure with hetero rings bridged together allows the energy of the host due to thermal motion to be consumed only for light emission but not for other things. Moreover, a heterocyclic compound having spirobisfluorene and heteroaryl has high triplet energy and achieves thermal stability.

The heterocyclic compound has spirobisfluorene with hole transfer properties and heteroaryl with hole or electron transfer properties. Especially, the heterocyclic compound has bipolarity involving the properties of both holes and electrons by having spirobisfluorene with hole transfer properties and heteroaryl with electron transfer properties, and therefore has electric stability against holes and electrons. Also, a host material with a spirobisfluorene compound with hole transfer properties bound to a material with electron transfer properties may be used to optimize the lifetime and efficiency of an organic light emitting layer. The material with electron transfer properties may have a heteroaryl group. Thus, the use of a heterocyclic compound with electric stability against holes and electrons as a host for the light emitting layer can increase the light emission area of the light emitting layer and therefore improve the lifetime of the device.

It will be apparent to those skilled in the art that various modifications and variations can be made in the organic light emitting display device of the present invention without departing from the spirit or scope of the invention. Thus, it is intended that the present invention cover the modifications and variations of the present invention provided they come within the scope of the appended claims and their equivalents.

What is claimed is:
1. A heterocyclic compound represented by the following Chemical Formula 1:

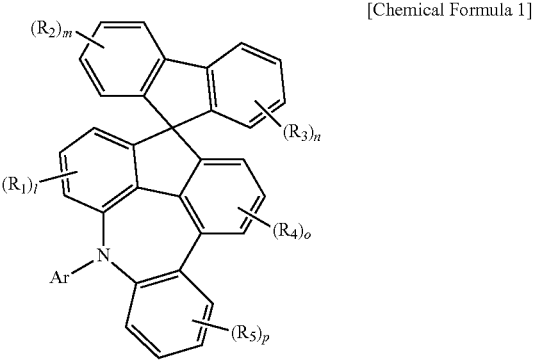

[Chemical Formula 1]

where R₁ to R₅ are independently one among hydrogen, deuterium, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l and o are an integer between 0 and 3, and m, n, and p are an integer between 0 and 4, wherein, if any of l, m, n, o, and p has a value of 2 or more, the corresponding R is the same with each other or if any of l, m, n, o, and p has a value of 2 or more, the corresponding R is different from each other, and Ar is a substituted or unsubstituted aryl group having to 30 carbon atoms or a substituted or unsubstituted heteroaryl group having 2 to 30 carbon atoms.

2. The heterocyclic compound of claim 1, wherein the heterocyclic compound includes one among the following compounds:

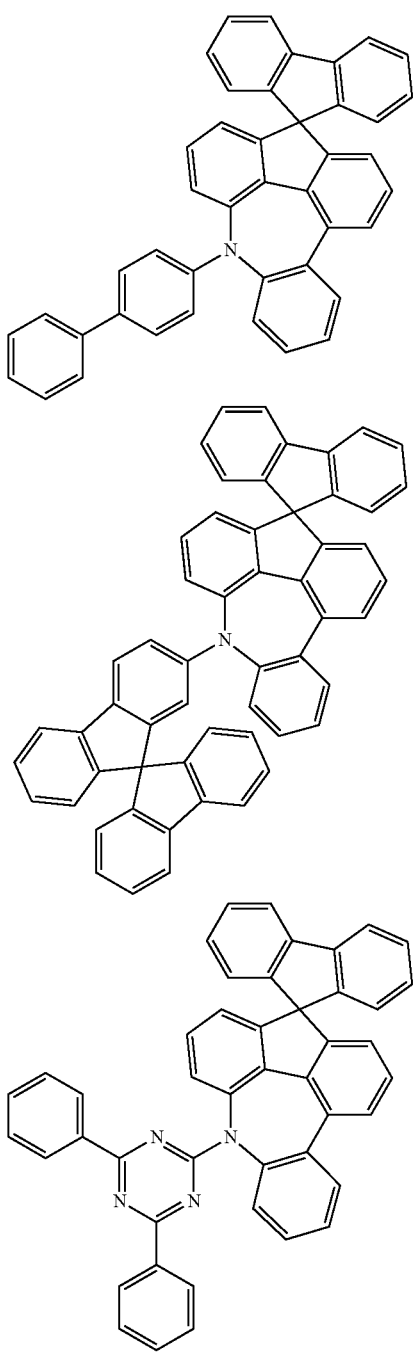

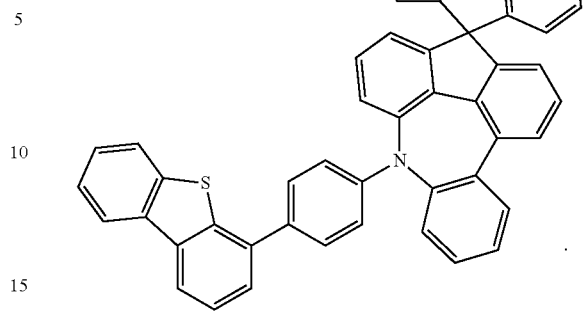

3. An organic light emitting display device, comprising:
an anode;
an organic layer on the anode; and
a cathode on the organic layer,
wherein the organic layer includes the heterocyclic compound according to any one of claims 1 and 2.

4. The organic light emitting display device of claim 3, wherein the organic layer includes a light emitting layer.

5. The organic light emitting display device of claim 4, wherein a host for the light emitting layer includes the heterocyclic compound.

6. The organic light emitting display device of claim 4, wherein the heterocyclic compound includes a compound having hole transfer properties and a material having electron transfer properties.

7. The organic light emitting display device of claim 3, wherein the light emitting layer includes a host and a dopant, and the triplet energy of the organic layer in the host is equal to or greater than 2.5 eV.

8. The organic light emitting display device of claim 3, wherein the organic layer includes at least one among a hole transport layer, an electron blocking layer, a hole blocking layer, and an electron transport layer, and the at least one among the hole transport layer, the electron blocking layer, the hole blocking layer, and the electron transport layer includes the heterocyclic compound.

9. The organic light emitting display device of claim 3, wherein an organic light emitting display device having the heterocyclic compound has a higher triplet energy, reduced operating voltage, and increased lifetime, as compared with an organic light emitting display device without the heterocyclic compound.

* * * * *